United States Patent [19]
Dorn

[11] Patent Number: 6,107,052
[45] Date of Patent: Aug. 22, 2000

[54] ENZYMATIC MEASUREMENT OF MYCOPHENOLIC ACID

[75] Inventor: Allan R. Dorn, Carmel, Ind.

[73] Assignee: Roche Diagnostics Corporation, Indianapolis, Ind.

[21] Appl. No.: 09/328,741

[22] Filed: Jun. 9, 1999

[51] Int. Cl.$^7$ ................................ C12Q 1/26; C12Q 1/00
[52] U.S. Cl. ................................ 435/25; 435/4; 435/975; 514/374
[58] Field of Search ................................ 435/25, 4, 975; 514/374

[56] References Cited

U.S. PATENT DOCUMENTS

| | | | |
|---|---|---|---|
| 4,753,935 | 6/1988 | Nelson et al. | 514/233.5 |
| 5,380,879 | 1/1995 | Sjogren | 549/310 |
| 5,444,072 | 8/1995 | Patterson et al. | 514/320 |
| 5,665,583 | 9/1997 | Collart et al. | 435/191 |
| 5,807,876 | 9/1998 | Armistead et al. | 514/374 |

FOREIGN PATENT DOCUMENTS

| | | | |
|---|---|---|---|
| WO 94/01105 | 1/1994 | WIPO | A61K 31/35 |
| WO 94/12184 | 6/1994 | WIPO | A61K 31/535 |
| WO 96/02004 | 1/1996 | WIPO | G01N 33/94 |
| WO 99/33996 | 7/1999 | WIPO | C12N 15/53 |

OTHER PUBLICATIONS

Fleming et al; "Biochemistry", V.35(22), p 6990–6997, Jun. 4, 1996.

Anderson, J. H., et al., "Inosinic Acid Dehydrogenase of Sarcoma 180 Cells," The Journal of Biological Chemistry 243 (18) 4762–4768 (1968).

Babson, A. L., et al., "Kenetic Colorimetric Measurement of Serum Lactate Dehydrogenase Activity," Clinical Chemistry 19 (7): 766–769 (1973).

Beal, J. L., et al., "Evaluation of an Immunoassay (EMIT) for Mycophenolic Acid in Plasma From Renal Transplant Recipients Compared With a High–Performance Liquid Chromatography Assay," Therapeutic Drug Monitoring 20:685–690 (1998).

Carr, S. J., et al., "Characterization of Human Type I and Type II IMP Dehydrogenases," The Journal of Biological Chemistry 268 (36):27286–27290 (1993).

Collart, F. R., et al., "Cloning and Sequence Analysis of the Human and Chinese Hamster Inosine–5'–monophosphate Dehydrogenase cDNAs," The Journal of Biological Chemistry 263 (30):15769–15772 (1988).

Emit(TM) Mycophenolic Acid Assay package insert, Behring Diagnostics Inc., San Jose, CA (1996).

Epinette, W. W., et al., "Mycophenolic acid for psoriasis," Journal of the American Academy of Dermatology 17 (6):962–971 (1987).

Fleming, M. A., "Inhibition of IMPDH by Mycophenolic Acid: Dissection of Forward and Reverse Pathways Using Capillary Electrophoresis," Biochemistry 35:6990–6997 (1996).

Glesne, D. A., et al., "Cloning and Sequence of the Human Type II IMP Dehydrogenase Gene," Biochem. Biophys. Res. Commun. 205 (1):537–544 (1994).

(List continued on next page.)

Primary Examiner—Louise N. Leary
Attorney, Agent, or Firm—Marilyn L. Amick; Roche Diagnostics Corporation

[57] ABSTRACT

The present invention provides a method for the enzymatic measurement of mycophenolic acid and other IMPDH inhibitors in biological samples.

The present invention also provides assay reagents and packaged kits useful for performing enzymatic measurement of mycophenolic acid and other IMPDH inhibitors in biological samples.

6 Claims, 5 Drawing Sheets

OTHER PUBLICATIONS

Griesmacher, A., et al., "Inhibition of Inosine Monophosphate Dehydrogenase Activity by the Plasma of Heart Transplant Recipients Receiving Mycophenolate Mofetil," Ludwig Boltzmann Institute for Cardiosurgical Research at the Institute of Laboratory Diagnostics of the Kaiser–Franz–Josef–Hospital 104:537–541 (1998).

Hager, P. W., et al., "Recombinant Human Inosine Monophosphate Dehydrogenase Type I and Type II Proteins," Biochemical Pharmacology 49 (9):1323–1329 (1995).

Jones, C. E., et al., "High–performance liquid chromatography determination of mycophenolic acid and its glucuronide metabolite in human plasma," Journal of Chromatography B 708:229–234 (1998).

Jones, D. F. et al., "Microbial Modification of Mycophenolic Acid," J. Chem. Soc. (C):1725–1737 (1970).

Konno, Y., et al., "Expression of Human IMP Dehydrogenase Types I and II in *Escherichia coli* and Distribution in Human Normal Lymphocytes and Leukemic Cell Lines," The Journal of Biological Chemistry 266 (1):506–509 (1991).

Langman, L. J., et al., "Blood Distribution of Mycophenolic Acid," Therapeutic Drug Monitoring 16:602–607 (1994).

Lee, W. A., "Bioavailability Improvement of Mycophenolic Acid Through Amino Ester Derivatization," Pharmaceutical Research 7 (2):161–166 (1990).

Magasanik, B., et al., "Enzymes Essential for the Biosynthesis of Nucleic Acid Guanine; Inosine 5'–Phosphate Dehydrogenase of Aerobacter Aerogenes," J. Biol. Chem. 226:339–350(1957).

Natsumeda, Y., et al., "Two Distinct cDNAs for Human IMP Dehydrogenase," The Journal of Biological Chemistry 265 (9):5292–5295 (1990).

Nelson, P. H., et al., "Synthesis and Immunosuppressive Activity of Some Side–Chain Variants of Mycophenolic Acid," J. Med. Chem. 33:833–838 (1990).

Noto, T., et al., "A Turidimetric Bioassay Method For Determination Of Mycophenolic Acid," The Journal of Antibiotics XXIII (2):96–98 (1970).

Nowak, I., et al., "Mycophenolic Acid to Human Serum Albumin: Characterization and Relation to pharmacodynamics," Clinical Chemistry 41 (7):1011–1017 (1995).

Schutz, E., et al., "Identification of an Active Metabolite of Mycophenolic Acid in Plasma of Liver Transplant Recipients," Hepatology (in press, 1998).

Schutz, et al., "Therapeutic Drug Monitoring of Mycophenolic Acid: Comparison of HPLC and Immunoassay Reveals New MPA Metabolites," Transplantation Proceedings 30:1185–1187 (1998).

Schutz, E., et al., "Identification of a Pharmacology Active Metabolite of Mycophenolic Acid in Plasma of Transplant Recipients Treated with Mycophenolate Mofetil," Clinical Chemistry 45 (3):419–422 (1999).

Tett, S. E., et al., "Evaluation of an immunoassay for mycophenolic acid in plasma compared with a HPLC–UV assay," Clinical Chemistry 44(6):A96–A97 (1998).

Yatscoff, R. W., et al., "Pharmacodynamic monitoring of immunosuppressive drugs," Clinical Chemistry 44 (2):428–432 (1998).

Zimmermann, A. G., et al., "Characterization of the Human Inosine–5'–monophosphate Dehydrogenase Type II Gene," The Journal of Biological Chemistry 270 (12) 6808–6814 (1995).

MPA

M-1

M-2

M-3

ENZYMATIC MEASUREMENT OF MYCOPHENOLIC ACID

BACKGROUND OF THE INVENTION

1. Field of the Invention

This invention relates generally to the field of measuring therapeutic drugs in biological samples. More specifically, it relates to a method for the enzymatic measurement of mycophenolic acid and other IMPDH inhibitors in a biological sample.

2. Description of the Related Art

The measurement of mycophenolic acid is of clinical significance. Mycophenolic acid is an immunosuppressive drug used to prevent rejection of transplanted organs, and the monitoring of mycophenolic acid is suggested to improve therapeutic efficacy and to minimize adverse side effects of the drug.

Mycophenolic acid is produced by the fermentation of several penicillium species. It has a broad spectrum of activities, specific mode of action, and is tolerable in large doses with minimal side effects, Epinette et al, *Journal of the American Academy of Dermatology* 17(6):962–971 (1987). Mycophenolic acid has been shown to have antitumor, antiviral, antipsoriatric, immunosuppressive and anti-inflammatory activities, Lee et al., *Pharmaceutical Research* 7(2):161–166 (1990), along with antibacterial and antifungal activities, Nelson, P. H. et al., *Journal of medicinal Chemistry* 33(2):833–838 (1990). MPA acts by inhibiting inosine-5'-monophosphate dehydrogenase (IMPDH), a key enzyme in the de novo synthesis of purine nucleotides. Since T and B lymphocytes depend largely upon this de novo synthesis, mycophenolic acid is able to inhibit lymphocyte proliferation, which is a major factor of the immune response.

Inosine-5'-monophosphate dehydrogenase (EC 1.1.1.205) catalyzes the NAD-dependent oxidation of inosine-5'-monophosphate (IMP) to xanthosine-5'-monophosphate (XMP), Magasanik, B. et al., *J Biol. Chem.*226:339–350 (1957) and Jackson et al., *Nature* 256:331–333 (1975). The enzyme follows an ordered Bi—Bi reaction sequence of substrate and cofactor binding and product release. First, IMP binds to IMPDH. This is followed by the binding of the cofactor NAD. The reduced cofactor, NADH, is then released from the product, followed by the product, XMP. This mechanism differs from that of most other known NAD-dependent dehydrogenases, which have either a random order of substrate addition or require NAD to bind before the substrate.

Two isoforms of human IMPDH, designated type I and type II, have been identified and sequenced, Collart et al., *J Biol. Chem.*263:15769–15772 (1988) and Natsumeda et al., *J Biol. Chem.*265:5292–5295 (1990). Each isoform is 514 amino acids, and both isoforms share 84% sequence identity. Both IMPDH type I and type II form active tetramers in solution, with subunit molecular weights of 56 kDa, Yamada et al., *Biochemistry* 27:2737–2745 (1988).

The morpholinoethyl ester of mycophenolic acid, morpholinoethyl E-6-(1,3-dihydro-4-hydroxy-6-methoxy-7-methyl-3-oxo-5-isobenzofuranyl)-4-methyl-4-hexenoate (MPA-M) is hydrolyzed in vivo to mycophenolic acid. Administration of mycophenolic acid in the form of this ester, also known as mycophenolate mofetil (MMF), greatly improves mycophenolic acid's bioavailability. MPA-M has a number of other favorable pharmaceutical characteristics, including its stability at pH 2–5 and its good solubility at low pH indicating rapid dissolution in the upper gastro-intestinal tract, Lee, et al., supra.

When used in combination therapy with cyclosporin A, MPA-M and cyclosporin A may have a synergistic mode of action. Cyclosporin A has a selective effect on T cells, but does not suppress B cell antibody production activity, while mycophenolic acid has an anti-proliferative effect on both T and B cells. Combined cyclosporin A/MPA-M therapy may increase survival time and allow for use of lower doses of cyclosporin A, which would reduce the side effects associated with cyclosporin A, primarily nephrotoxicity.

Mycophenolic acid is metabolized by conjugation with glucuronic acid forming mycophenolic acid glucuronide (MPAG). Two additional metabolites of MPA have been described by Schutz, E. et al., *Clinical Chemistry* 45(3):419–422 (1999), the 7-O-glucoside of MPA (M-1) and the acyl glucuronide of MPA (M-2). Schutz et al. measured the inhibition of recombinant human IMPDH-II by MPA, MPAG, M-1 and M-2 using purified preparations of the metabolites and found that M-2 exhibited a concentration-dependent inhibition of IMPDH-II similar to that obtained with MPA. However, different preparations of M-2 were not consistent in their ability to inhibit IMPDH-II. The metabolite M-2 is likely to be a mixture of isomers since it is known that acyl glucuronides undergo intramolecular rearrangement at physiological pH. Also, acyl glucuronides can hydrolyze back to MPA. Note that a mixture of isomers of M-2 will all equally cross react with an antibody but may not equally inhibit IMPDH. In light of the Schutz findings, it may not be surprising that measurements of MPA using the method of the present invention correlate well with results obtained via HPLC (r=0.994).

Because mycophenolic acid is a potent biologically active material, an effective assay would be useful in monitoring its bioavailability. In addition, it may be important to monitor therapeutic drug levels, i.e., optimal drug levels necessary for adequate immunosuppression. Since MPA-M is hydrolyzed to mycophenolic acid, an assay for mycophenolic acid would allow monitoring of MPA-M dosages.

The use of high-performance liquid chromatography (HPLC) to determine the concentration of mycophenolic acid in human plasma is described in Jones, C. E. et al., *Journal of Chromatography* B 708:229–234 (1998).

Jones et al., *J Chem. Soc.* (C) 1725–1737 (1970) discloses numerous transformations that mycophenolic acid undergoes when incubated with select microorganisms.

Nelson, P. H. et al., U.S. Pat. No. 4,753,935 (1988), describes the morpholinoethyl ester of mycophenolic acid, its pharmaceutical uses and post-dosage monitoring by HPLC of the recipient's plasma concentration of mycophenolic acid.

An immunoassay for mycophenolic acid using monoclonal antibodies to mycophenolic acid is described in Alexander, S. et al., PCT Publication No. WO 96/02004 (1996).

Problems of specificity with the immunoassay are discussed in Tett, S. E. et al., *Clinical Chemistry* 44(6):A96–A97 (1998). The authors compared results obtained on transplant patients using a commercial EMIT® immunoassay (Behring Diagnostics) with those obtained HPLC-UV and found up to 95% overestimation with the immunoassay among mid-range concentrations.

The inhibition of IMPDH by mycophenolic acid is described by Anderson, J. H. et al., *Journal of Biological Chemistry* 243(18):4762–4768 (1968). Inhibitors of IMPDH are also described in U.S. Pat. Nos. 5,380,879, 5,444,072 and 5,807,876 and in PCT publications WO 94/01105 and WO 94/12184.

Yatscoff, R. W. et al., *Clinical Chemistry* 44(2):428–432 (1998) reports on the pharmacodynamic monitoring of mycophenolic acid in human plasma by measuring the residual level of IMPDH activity present in the patient's own lymphocytes. This approach measures the patient's own biological response to the drug. It does not provide a method to directly quantitate the drug in the patient's plasma.

The cloning and expression of human IMPDH in *E. coli* has been described by Konno, Y. et al., *J. Biol. Chem* 266(1):506–509 (1991). Collart, F. R. et al., U.S. Pat. No. 5,665,583 (1997) also describe the cloning and expression in *E. coli* of human IMPDH.

SUMMARY OF THE INVENTION

The present invention is based upon the uncompetitive inhibition of the enzyme inosine-5'-monophosphate dehydrogenase (IMPDH) by mycophenolic acid (MPA). IMPDH catalyzes the following reaction:

inosine monophosphate

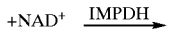

xanthosine monophosphate+NADH

The rate of formation of NADH (reduced nicotinamide adenine dinucleotide) can be measured by monitoring the change in absorption at a wavelength of 340 nm, i.e., the characteristic absorption region of NADH, and this change in absorption can then be correlated to the MPA concentration.

Mycophenolic acid binds to the active site of IMPDH but does not compete with substrate. One of the acyl glucuronide metabolites of mycophenolic acid may inhibit the reaction equally as well as mycophenolic acid.

In an assay according to the present invention, mycophenolic acid present in a serum or plasma sample inhibits the above reaction, the measurement of which can be monitored spectrophotometrically at a wavelength of 340 nm. Thus, the concentration of mycophenolic acid in a sample is inversely proportional to the absorbance of NADH at 340 nm.

Similarly, the assay of the present invention may be used to determine levels of other IMPDH inhibitors in serum or plasma, such as the therapeutic IMPDH inhibitors described by Armistead et al. in U.S. Pat. No. 5,807,876 (1998).

Another aspect of the present invention relates to a kit for conducting an assay for the determination of mycophenolic acid comprising in packaged combination a first reagent composition comprising IMPDH and IMP and a second reagent composition comprising NAD. Alternatively, a similarly comprised kit is also useful for conducting an assay for the determination of other IMPDH inhibitors.

The IMPDH enzyme preferred for use is a recombinant IMPDH-II enzyme from human T lymphocytes.

BRIEF DESCRIPTION OF THE DRAWINGS

FIG. 2(*a*) shows the breakdown of MMF into MPA, MPAG and M1, and FIG. 2(*b*) shows the breakdown of MMF into MPA, M1 and M2 metabolites.

DETAILED DESCRIPTION OF THE INVENTION

The following definitions and general parameters are set forth to illustrate and define the meaning and scope of the various terms used to describe the invention herein.

Sample suspected of containing the analyte: Any sample that is reasonably suspected of containing the analyte, i.e., mycophenolic acid or other IMPDH inhibitor, can be analyzed by the method of the present invention. The sample is typically an aqueous solution such as a body fluid from a host, for example, urine, whole blood, plasma, serum, saliva, semen, stool, sputum, cerebral spinal fluid, tears, mucus or the like, but preferably is plasma or serum. The sample can be pretreated if desired and can be prepared in any convenient medium that does not interfere with the assay. An aqueous medium is preferred.

Measuring the amount of mycophenolic acid: Quantitative, semi-quantitative and qualitative methods as well as all other methods for determining mycophenolic acid are considered to be methods of measuring the amount of mycophenolic acid. For example, a method that merely detects the presence or absence of mycophenolic acid in a sample suspected of containing mycophenolic acid is considered to be included within the scope of the present invention. The terms "detecting" and "determining", as well as other common synonyms for measuring, are contemplated within the scope of the present invention.

The determination of MPA according to the present invention may be conducted by a rate-assay method wherein change in absorbance of NADH per unit time is measured or by an end-point method wherein the reaction is quenched after a certain period of time has elapsed. The method can easily be applied to automated analyzers for laboratory or clinical analysis. Other methods for measuring NADH are also contemplated, for example, the reduction of NAD is coupled to the reduction of a tetrazolium salt, 2-p-nitrophenyl-5-phenyl tetrazolium chloride (INT), with phenazine methosulfate serving as an intermediate electron carrier, as described in Babson, A. L. et al, *Clinical Chemistry* 19(7):766–769 (1973).

Figure 3:
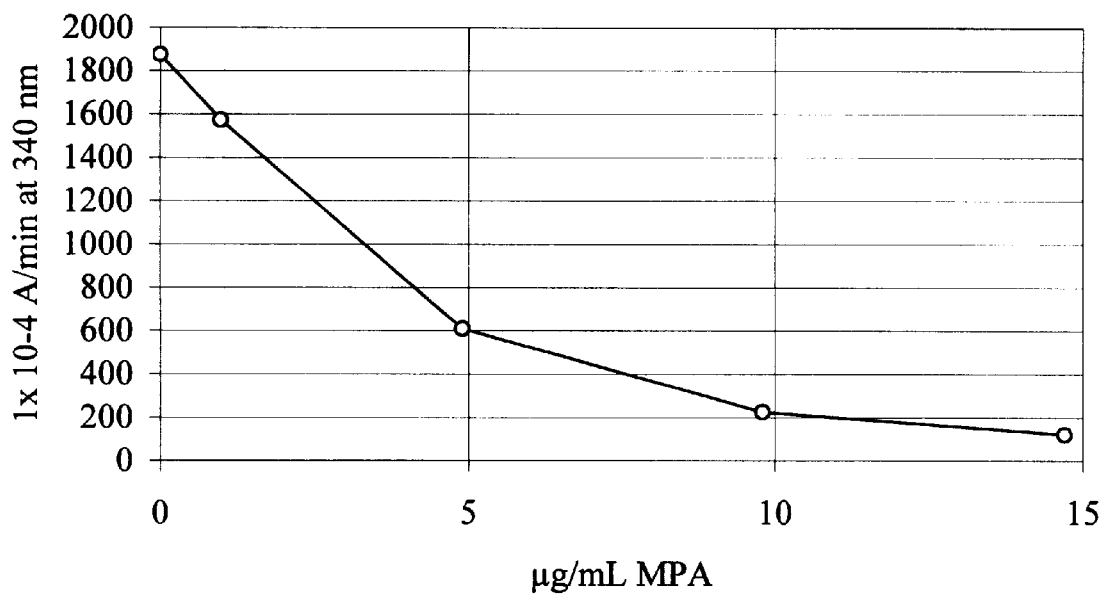
FIG. 3 is a plot of the concentration of mycophenolic acid versus the change in absorbance at 340 nm.
Figure 4:
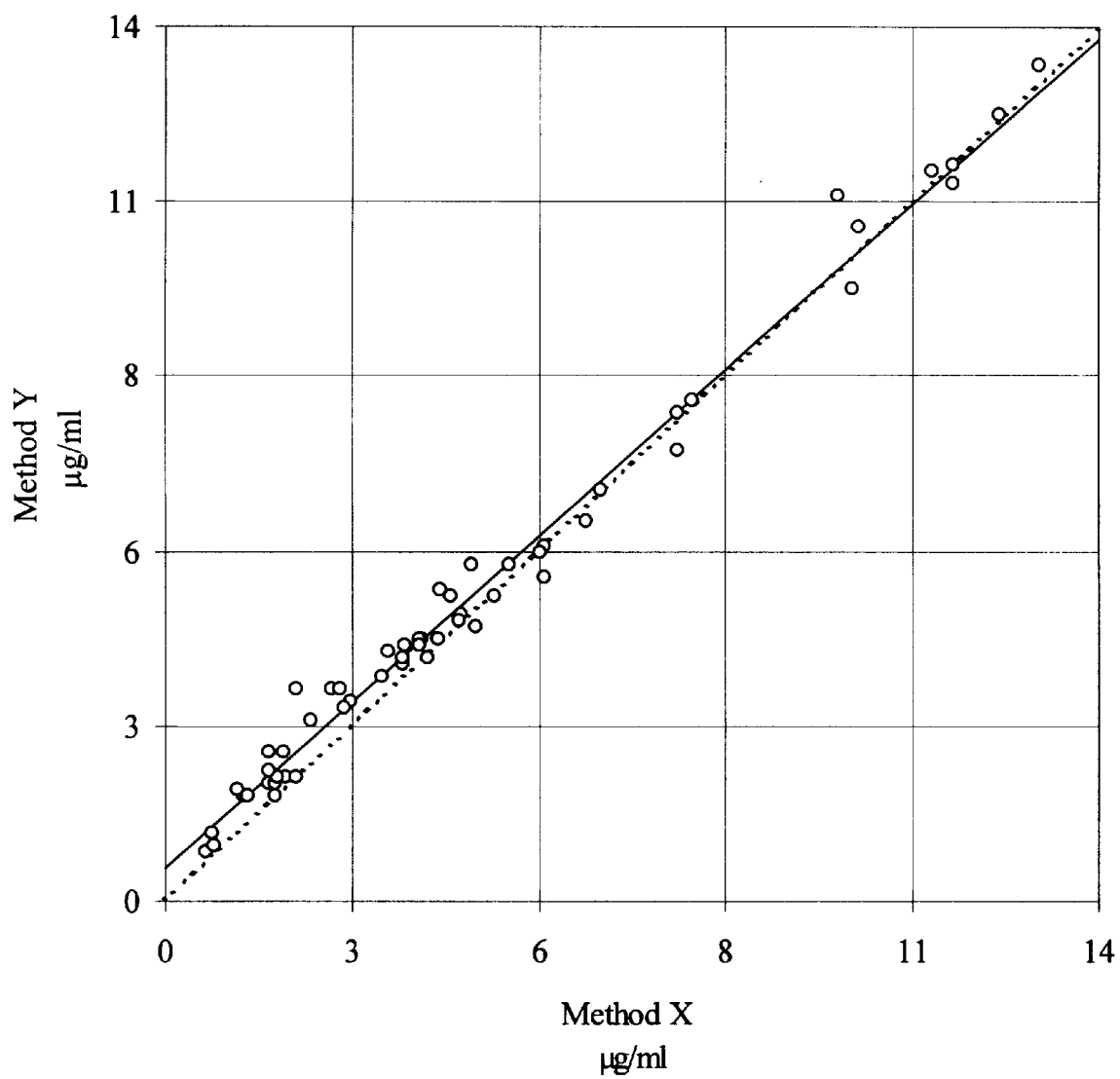
FIG. 4 is a method comparison plot of values obtained on plasma samples comparing the method of the present invention against HPLC as a reference method.

Calibration material means any standard or reference material containing a known amount of the analyte to be measured. The sample suspected of containing the analyte and the calibration material are assayed under similar conditions. Analyte concentration is then calculated by comparing the results obtained for the unknown specimen with results obtained for the standard. This is commonly done by constructing a calibration curve such as in FIG. 3.

Ancillary materials: Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumin, or surfactants, particularly non-ionic surfactants, or the like.

IMPDH refers to the enzyme inosine-5'-monophosphate dehydrogenase, EC 1.1.1.205, which catalyzes the formation of xanthine-5'-monophosphate from inosine-5'-monophosphate. The present invention contemplates the use of IMPDH from natural or recombinant sources, and either isoform or a mixture of isoforms may be used.

It is to be understood that any reference throughout the specification and claims to mycophenolic acid is meant to cover mycophenolic acid as well as its biologically active and therapeutically active metabolites and derivatives, which behave in a biological sense, i.e. via IMPDH inhibition, as mycophenolic acid.

Another aspect of the present invention relates to kits useful for conveniently performing the assay methods of the invention for the determination of mycophenolic acid. To enhance the versatility of the subject invention, reagents useful in the methods of the invention can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents.

The kit of the present invention contains the reagents IMPDH enzyme, IMP substrate and NAD substrate. The IMPDH, IMP and NAD are commonly combined with an appropriate buffer and ancillary materials and then packaged. The reagents may remain in liquid form or lyophilized. The kit can further comprise other packaged calibration materials. In a preferred embodiment, the kit comprises IMPDH, IMP, NAD and a buffer.

In the examples below, two reagents were prepared, one comprising IMPDH and the other comprising NAD. In the examples, IMP was combined with the IMPDH reagent due to the known stabilizing effects of a substrate on an enzyme; however, alternatively the IMP could be incorporated in the NAD reagent instead. Other combinations and perturbations may also suggest themselves to those skilled in the art.

A more complete understanding of the present invention will be obtained by reference to the following non-limiting examples.

EXAMPLES

Preparation of IMPDH Reagent

One hundred milliliters (ml) of a first reagent composition were prepared as follows. Approximately 80 ml deionized water were dispensed into a container and 3.37 grams of 3-[N-tris-(hydroxymethyl) methylamino]-2-hydroxy-propanesulfonate, Na (TAPSO) were added and completely dissolved. Next, 4.91 grams of sodium acetate were added to the container and dissolved, followed by 0.037 gram dithiothreitol (DTT), 0.019 gram inosine monophosphate (IMP), 0.134 gram $Na_2EDTA$ and 0.10 gram SUTTOCIDE A (GAF Chemicals Corp.). The pH was adjusted to 8.0 with 0.1N hydrochloric acid (HCl). The volume was adjusted to 100 ml with deionized water. Finally, 0.034 units of highly purified recombinant human IMPDH-II was added and dissolved completely.

The procedure used for cloning and purification of IMPDH-II is described in Carr, S. F. et al., *J. Biological Chemistry* 268(36):27286–27290 (1993), the content of which is herein incorporated by reference. Cloning of IMPDH is also described in Collart, F. R. et al., U.S. Pat. No. 5,665,583 (1997).

Effective amount of reagent components are variable depending on specific needs and may be adjusted by simple laboratory experimentation to meet particular assay requirements.

Preparation of NAD Reagent

One hundred ml of a second reagent composition were prepared as follows. Approximately 80 ml deionized water were dispensed into a container and 1.82 grams of N-[2-acetamido]-2-aminoethanesulfonic acid (ACES) were added and completely dissolved. The pH was adjusted to 6.0 with 2N sodium hydroxide (NaOH). Then 0.166 gram nicotinamide adenine dinucleotide (NAD) was added, followed by 0.095 gram sodium azide and 0.1 gram SUTTOCIDE A. The volume was adjusted to 100 ml with deionized water.

Preparation of Mycophenolic Acid Standards

Mycophenolic acid standards were prepared from commercially available material (Sigma Chemical). The MPA was approximately 98% pure by thin layer chromatography and HPLC, and the identity of MPA was consistent with structure by NMR. A set of MPA standards was prepared with normal human plasma (potassium/EDTA) pooled from several donors. The MPA was weighed out and dissolved in the plasma pool to target concentrations of 0.98 $\mu$g/ml, 4.9 $\mu$g/ml, 9.8 $\mu$g/ml and 14.7 $\mu$g/ml. These standards were used to calibrate the instrument used in the assay below.

Assay for Mycophenolic Acid

Mycophenolic acid determinations were made using an HITACHI 717 analyzer (Roche Diagnostics Corp., Indianapolis). The primary wavelength used was 340 nm and the secondary wavelength was 700 mn. The analyzer was programmed to dispense 3 $\mu$l of sample into a cuvette incubated in a waterbath at 37° C. Then 250 $\mu$l of the IMPDH-II reagent composition was added to the sample, mixed and allowed to incubate for 5 minutes, after which time 50 $\mu$l of the NAD reagent composition was added and mixed. The difference in absorbance at 340 nm was calculated from the initial addition of the second reagent 5 minutes following the second reagent composition addition. The absorbance rate at 340 nm is inversely proportional to the mycophenolic acid concentration in the sample. Concentrations of MPA are calculated by the instrument by comparing the rate of production of NADH by the unknown sample with the rate of production of NADH by the standards containing known amounts of MPA.

Comparison with HPLC

Figure 1:
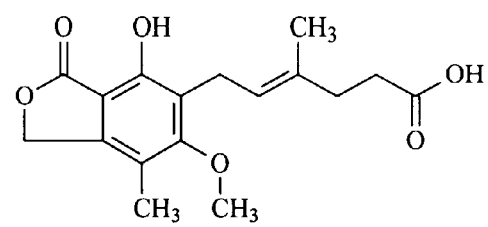
FIG. 1 shows the structures of MPA and the glucuronide metabolites of MPA.
Figure 1:
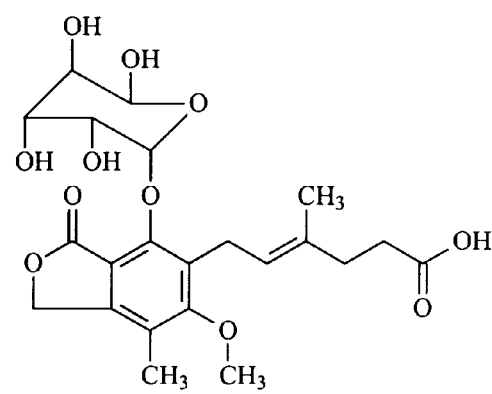
Figure 1:
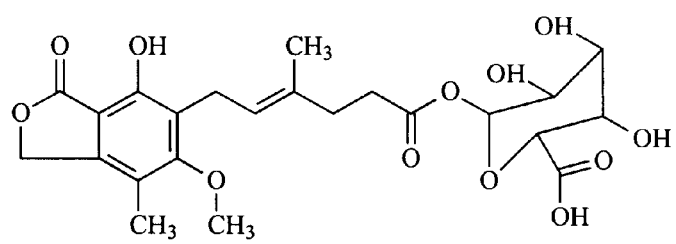
Figure 1:
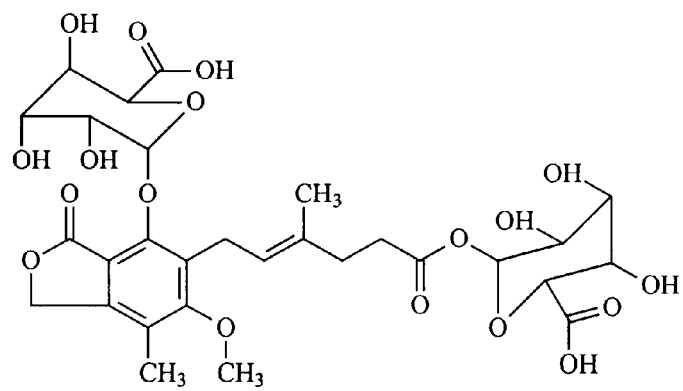
Figure 2:
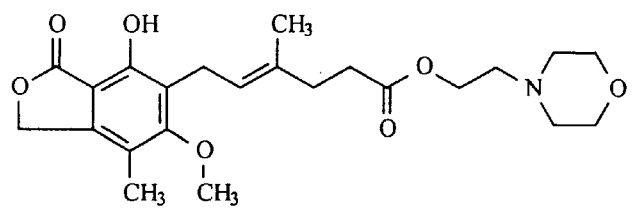
FIG. 2 illustrates metabolic breakdown pathways for MMF.
Figure 2:
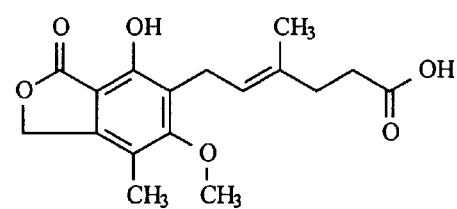
Figure 2:
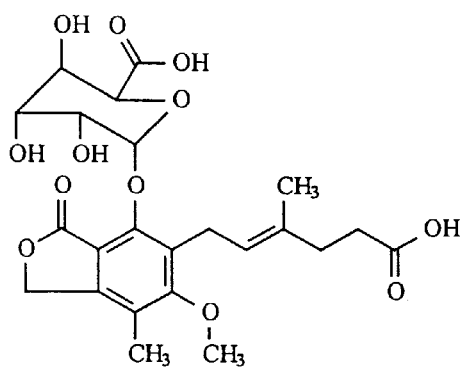
Figure 2:
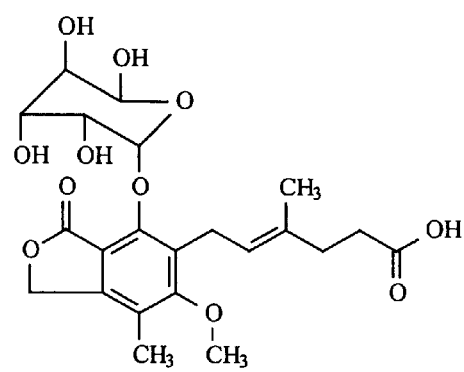
Figure 2:
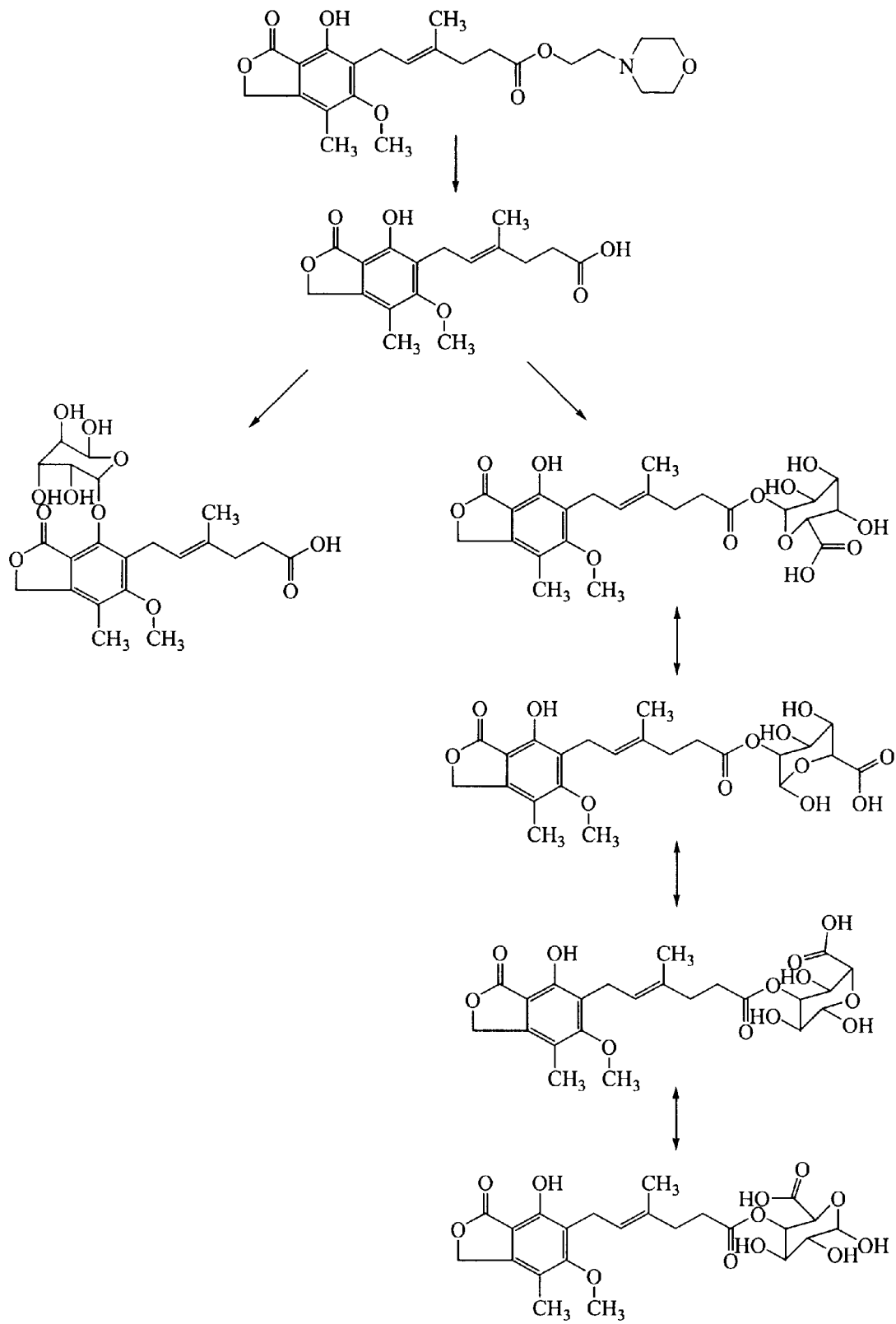

Plasma samples from a group of 55 human transplant patients were assayed for mycophenolic acid using the method of the present invention (Method Y). Results obtained were then compared with results obtained when assaying the patient samples for mycophenolic acid using HPLC as a reference method (Method X). The plasma samples used were obtained using EDTA anticoagulant, and the procedure used for Method Y was as described above. The HPLC method used is as is known to those skilled in the art (See Jones, C. E. al., Journal of Chromatography B 708:229–234 (1998) for representative method.) Results obtained are by the two methods are listed below, and a comparison plot of the values obtained by the two methods is shown in FIG. 2. Least squares linear regression analysis gave a correlation coefficient of 0.994 and an equation of Y=0.957X+0.515.

| Sample No. | Method X | Method Y |
| --- | --- | --- |
| 1 | 10.3 | 9.8 |
| 2 | 11.5 | 11.7 |
| 3 | 3.57 | 4.1 |
| 4 | 7.89 | 8.0 |
| 5 | 13.1 | 13.4 |
| 6 | 0.59 | 0.8 |
| 7 | 0.71 | 0.9 |
| 8 | 1.16 | 1.7 |
| 9 | 1.23 | 1.7 |
| 10 | 1.53 | 1.9 |

-continued

| Sample No. | Method X | Method Y |
|---|---|---|
| 11 | 3.23 | 3.6 |
| 12 | 2.76 | 3.2 |
| 13 | 4.27 | 4.9 |
| 14 | 1.53 | 2.4 |
| 15 | 3.32 | 4.0 |
| 16 | 3.81 | 4.2 |
| 17 | 4.63 | 4.4 |
| 18 | 3.93 | 3.9 |
| 19 | 5.67 | 5.7 |
| 20 | 4.93 | 4.9 |
| 21 | 6.53 | 6.6 |
| 22 | 1.62 | 1.9 |
| 23 | 3.53 | 3.8 |
| 24 | 3.54 | 3.9 |
| 25 | 2.65 | 3.1 |
| 26 | 1.77 | 2.0 |
| 27 | 1.07 | 1.8 |
| 28 | 2.48 | 3.4 |
| 29 | 1.95 | 3.4 |
| 30 | 1.76 | 2.4 |
| 31 | 0.7 | 1.1 |
| 32 | 1.65 | 2.0 |
| 33 | 2.17 | 2.9 |
| 34 | 2.61 | 3.4 |
| 35 | 1.55 | 2.1 |
| 36 | 3.8 | 4.2 |
| 37 | 4.41 | 4.6 |
| 33 | 4.06 | 4.2 |
| 39 | 5.14 | 5.4 |
| 40 | 10.1 | 11.3 |
| 41 | 1.63 | 1.7 |
| 42 | 4.4 | 4.5 |
| 43 | 5.61 | 5.6 |
| 44 | 11.8 | 11.5 |
| 45 | 3.8 | 4.1 |
| 46 | 4.11 | 5.0 |
| 47 | 1.95 | 2.0 |
| 48 | 5.66 | 5.2 |
| 49 | 12.5 | 12.6 |
| 50 | 6.3 | 6.1 |
| 51 | 4.57 | 5.4 |
| 52 | 7.67 | 7.8 |
| 53 | 10.4 | 10.9 |
| 54 | 11.8 | 12.4 |
| 55 | 7.67 | 7.5 |

While the present invention has been described with reference to the specific embodiments thereof, it should be understood by those skilled in the art that various changes may be made and equivalents may be substituted without departing from the true spirit and scope of the invent. For example, if increased assay sensitivity were desired, a person skilled in the art could use enzyme cycling for amplification of the primary enzyme reaction whereby the NADH produced in the primary reaction is used as the substrate in a secondary reaction.

In addition, other modifications may be made to adapt a particular situation, material, composition of matter, process, process step or steps, to the objective, spirit and scope of the present invention. All such modifications are intended to be within the scope of the claims appended hereto.

What is claimed is:

1. A method for determining mycophenolic acid in a biological sample comprising the steps of:

a. combining a sample suspected of containing mycophenolic acid with effective amounts of IMP, NAD and IMPDH under conditions suitable for IMPDH activity, b. monitoring the production of NADH, and c. comparing the production of NADH with the production of NADH by a sample containing a known amount of mycophenolic acid after being treated according to steps (a) and (b).

2. A method for determining an inhibitor of IMPDH in a biological sample comprising the steps of:

a. combining a sample suspected of containing said inhibitor of IMPDH with effective amounts of IMP, NAD and IMPDH under conditions suitable for IMPDH activity, b. monitoring the production of NADH, and c. comparing the production of NADH with the production of NADH by a sample containing a known amount of said therapeutic inhibitor of IMPDH after being treated according to steps (a) and (b).

3. A kit for conducting an assay for the determination of mycophenolic acid comprising in packaged combination:

a. a first reagent comprising effective amounts of IMPDH, IMP and a buffer, and b. a second reagent comprising effective amounts of NAD and a buffer.

4. The kit of claim 3, said kit further comprising a calibration reagent comprising a known amount of mycophenolic acid.

5. A kit for conducting an assay for the determination of an inhibitor of IMPDH comprising in packaged combination:

a. a first reagent comprising effective amounts of IMPDH, IMP and a buffer, and b. a second reagent comprising effective amounts of NAD and a buffer.

6. The kit of claim 5, said kit further comprising a calibration reagent comprising a known amount of mycophenolic acid.

* * * * *